(12) United States Patent
Tanner, Jr. et al.

(10) Patent No.: US 10,102,340 B2
(45) Date of Patent: Oct. 16, 2018

(54) SYSTEM AND METHOD FOR DYNAMIC HEALTHCARE INSURANCE CLAIMS DECISION SUPPORT

(71) Applicant: PokitDok, Inc., San Mateo, CA (US)

(72) Inventors: Theodore C. Tanner, Jr., San Mateo, CA (US); Colin E. Alstad, San Mateo, CA (US); W. Bryan Smith, San Mateo, CA (US); Denise K. Gosnell, San Mateo, CA (US); Virginia C. Harrison, San Mateo, CA (US)

(73) Assignee: PokitDok, Inc., San Mateo, CA (US)

( * ) Notice: Subject to any disclaimer, the term of this patent is extended or adjusted under 35 U.S.C. 154(b) by 0 days.

(21) Appl. No.: 15/174,595

(22) Filed: Jun. 6, 2016

(65) Prior Publication Data

US 2017/0351821 A1    Dec. 7, 2017

(51) Int. Cl.
*G06F 19/00* (2018.01)
*G16H 50/20* (2018.01)

(52) U.S. Cl.
CPC ............ *G06F 19/328* (2013.01); *G06F 19/00* (2013.01); *G16H 50/20* (2018.01)

(58) Field of Classification Search
CPC .... G06Q 50/22; G06Q 40/08; G06F 19/3418; G06F 19/3462; G06F 19/00; G06F 19/3456; G06F 19/321; G06F 17/30386; G06F 19/3481; G06F 19/3487; G06F 19/3475; G06F 17/14; G06F 17/142; G06F 19/322; G06F 19/328; G16H 50/20; G16H 15/00; G16H 40/63; G16H 10/60; G16H 50/50; G16H 10/40; G16H 40/20; G16H 40/40; G16H 50/70; G16H 20/13; G16H 40/67; G16H 50/30; G16H 50/80; G16H 80/00

See application file for complete search history.

(56) References Cited

U.S. PATENT DOCUMENTS

| | | | |
|---|---|---|---|
| 5,872,021 A | 2/1999 | Matsumoto et al. |
| 6,546,428 B2 | 4/2003 | Baber et al. |
| 7,386,565 B1 | 6/2008 | Singh et al. |
| 7,917,378 B2 | 3/2011 | Fitzgerald et al. |
| 7,917,515 B1 | 3/2011 | Lemoine |
| 7,970,802 B2 | 6/2011 | Ishizaki |
| 7,992,153 B2 | 8/2011 | Ban |
| 8,060,395 B1 | 11/2011 | Frasher et al. |
| 8,073,801 B1 | 12/2011 | Von Halle et al. |
| 8,095,975 B2 | 1/2012 | Boss et al. |
| 8,103,667 B2 | 1/2012 | Azar et al. |

(Continued)

FOREIGN PATENT DOCUMENTS

| GB | 2478440 | 10/2013 |
|---|---|---|
| WO | WO 2012/122065 | 9/2012 |

OTHER PUBLICATIONS

Ahlswede et al., *Network Information Flow*, IEEE Transactions on Information Theory, vol. 46, No. 4; Jul. 2000 (13 pgs.).

(Continued)

*Primary Examiner* — Joseph D Burgess
(74) *Attorney, Agent, or Firm* — DLA Piper LLP (US)

(57) ABSTRACT

A healthcare claims processing and decision support system and method are disclosed that allow for the pre-processing of the healthcare claims as well as a method to reduce much of this overhead and alerting the user to any errors that occur during the claims processing.

14 Claims, 8 Drawing Sheets

(56) References Cited

U.S. PATENT DOCUMENTS

| | | |
|---|---|---|
| 8,103,952 B2 | 1/2012 | Hopp |
| 8,203,562 B1 | 6/2012 | Alben et al. |
| 8,229,808 B1 | 7/2012 | Heit |
| 8,286,191 B2 | 10/2012 | Amini et al. |
| 8,359,298 B2 | 1/2013 | Schacher et al. |
| 8,364,501 B2 | 1/2013 | Rana et al. |
| 8,417,755 B1 | 4/2013 | Zimmer |
| 8,495,108 B2 | 7/2013 | Nagpal et al. |
| 8,515,777 B1 | 8/2013 | Rajasenan |
| 8,817,665 B2 | 8/2014 | Thubert et al. |
| 8,984,464 B1 | 3/2015 | Mihal et al. |
| 9,165,045 B2 | 10/2015 | Mok et al. |
| 9,208,284 B1 | 12/2015 | Douglass |
| 2002/0022973 A1 | 2/2002 | Sun et al. |
| 2002/0038233 A1 | 3/2002 | Shubov et al. |
| 2002/0165738 A1* | 11/2002 | Dang ............... G06F 19/328 705/3 |
| 2003/0055668 A1 | 3/2003 | Saran et al. |
| 2003/0097359 A1 | 5/2003 | Ruediger |
| 2003/0171953 A1 | 9/2003 | Narayanan et al. |
| 2003/0217159 A1 | 11/2003 | Schramm-Apple et al. |
| 2003/0233252 A1 | 12/2003 | Haskell et al. |
| 2004/0143446 A1 | 7/2004 | Lawrence |
| 2005/0010452 A1 | 1/2005 | Lusen |
| 2005/0071189 A1 | 3/2005 | Blake et al. |
| 2005/0102170 A1 | 5/2005 | Lefever et al. |
| 2005/0137912 A1 | 6/2005 | Rao et al. |
| 2005/0152520 A1* | 7/2005 | Logue ............... G06Q 20/14 379/114.14 |
| 2005/0182780 A1 | 8/2005 | Forman et al. |
| 2005/0222912 A1 | 10/2005 | Chambers |
| 2006/0036478 A1 | 2/2006 | Aleynikov et al. |
| 2006/0074290 A1 | 4/2006 | Chen et al. |
| 2006/0089862 A1 | 4/2006 | Anandarao et al. |
| 2006/0129428 A1 | 6/2006 | Wennberg |
| 2006/0136264 A1 | 6/2006 | Eaton et al. |
| 2007/0113172 A1 | 5/2007 | Behrens et al. |
| 2007/0118399 A1 | 5/2007 | Avinash et al. |
| 2007/0156455 A1 | 7/2007 | Tarino et al. |
| 2007/0174101 A1 | 7/2007 | Li et al. |
| 2007/0180451 A1 | 8/2007 | Ryan et al. |
| 2007/0214133 A1 | 9/2007 | Liberty et al. |
| 2007/0233603 A1 | 10/2007 | Schmidgall et al. |
| 2007/0260492 A1 | 11/2007 | Feied et al. |
| 2007/0276858 A1 | 11/2007 | Cushman et al. |
| 2007/0288262 A1 | 12/2007 | Sakaue et al. |
| 2008/0013808 A1 | 1/2008 | Russo et al. |
| 2008/0082980 A1 | 4/2008 | Nessland et al. |
| 2008/0091592 A1 | 4/2008 | Blackburn et al. |
| 2008/0126264 A1 | 5/2008 | Tellefsen et al. |
| 2008/0133436 A1 | 6/2008 | Di Profio |
| 2008/0288292 A1 | 11/2008 | Bi et al. |
| 2008/0295094 A1 | 11/2008 | Korupolu et al. |
| 2008/0319983 A1 | 12/2008 | Meadows |
| 2009/0083664 A1 | 3/2009 | Bay |
| 2009/0125796 A1 | 5/2009 | Day et al. |
| 2009/0192864 A1 | 7/2009 | Song et al. |
| 2009/0198520 A1 | 8/2009 | Piovanetti-Perez |
| 2009/0300054 A1 | 12/2009 | Fisher et al. |
| 2009/0307104 A1 | 12/2009 | Weng |
| 2009/0313045 A1 | 12/2009 | Boyce |
| 2010/0076950 A1 | 3/2010 | Kenedy et al. |
| 2010/0082620 A1 | 4/2010 | Jennings, III et al. |
| 2010/0088108 A1 | 4/2010 | Machado |
| 2010/0088119 A1 | 4/2010 | Tipirneni |
| 2010/0138243 A1 | 6/2010 | Carroll |
| 2010/0217973 A1 | 8/2010 | Kress et al. |
| 2010/0228721 A1 | 9/2010 | Mok et al. |
| 2010/0295674 A1 | 11/2010 | Hsieh et al. |
| 2010/0332273 A1 | 12/2010 | Balasubramanian et al. |
| 2011/0015947 A1 | 1/2011 | Erry et al. |
| 2011/0055252 A1 | 3/2011 | Kapochunas et al. |
| 2011/0071857 A1 | 3/2011 | Malov et al. |
| 2011/0137672 A1 | 6/2011 | Adams et al. |
| 2011/0218827 A1 | 9/2011 | Kennefick et al. |
| 2011/0270625 A1 | 11/2011 | Pederson et al. |
| 2012/0011029 A1 | 1/2012 | Thomas et al. |
| 2012/0035984 A1 | 2/2012 | Srinivasa et al. |
| 2012/0078940 A1 | 3/2012 | Kolluri et al. |
| 2012/0130736 A1 | 5/2012 | Dunston et al. |
| 2012/0158429 A1 | 6/2012 | Murawski et al. |
| 2012/0158750 A1 | 6/2012 | Faulkner et al. |
| 2012/0173279 A1 | 7/2012 | Nessa et al. |
| 2012/0245958 A1 | 9/2012 | Lawrence et al. |
| 2012/0246727 A1 | 9/2012 | Elovici et al. |
| 2012/0290320 A1 | 11/2012 | Kurgan et al. |
| 2012/0290564 A1 | 11/2012 | Mok et al. |
| 2013/0030827 A1 | 1/2013 | Snyder et al. |
| 2013/0044749 A1 | 2/2013 | Eisner et al. |
| 2013/0085769 A1 | 4/2013 | Jost et al. |
| 2013/0138554 A1 | 5/2013 | Nikankin et al. |
| 2013/0166552 A1 | 6/2013 | Rozenwald et al. |
| 2013/0204940 A1 | 8/2013 | Kinsel et al. |
| 2013/0304903 A1 | 11/2013 | Mick et al. |
| 2014/0046931 A1 | 2/2014 | Mok et al. |
| 2014/0056243 A1 | 2/2014 | Pelletier et al. |
| 2014/0059084 A1 | 2/2014 | Adams et al. |
| 2014/0088981 A1 | 3/2014 | Momita |
| 2014/0136233 A1 | 5/2014 | Atkinson et al. |
| 2014/0180727 A1* | 6/2014 | Freiberger ............ G07C 5/008 705/4 |
| 2014/0222482 A1 | 8/2014 | Gautam et al. |
| 2014/0244300 A1 | 8/2014 | Bess et al. |
| 2014/0249878 A1 | 9/2014 | Kaufman et al. |
| 2014/0278491 A1 | 9/2014 | Weiss |
| 2014/0358578 A1* | 12/2014 | Ptachcinski ........... G06Q 50/22 705/2 |
| 2014/0358845 A1 | 12/2014 | Mundlapudi et al. |
| 2015/0095056 A1 | 4/2015 | Ryan et al. |
| 2015/0112696 A1 | 4/2015 | Kharraz Tavakol |
| 2015/0142464 A1 | 5/2015 | Rusin et al. |
| 2015/0199482 A1* | 7/2015 | Corbin .................. G06Q 50/22 705/2 |
| 2015/0332283 A1 | 11/2015 | Witchey |
| 2016/0028552 A1 | 1/2016 | Spanos et al. |
| 2016/0055205 A1 | 2/2016 | Jonathan et al. |
| 2016/0253679 A1 | 9/2016 | Venkatraman et al. |
| 2016/0328641 A1 | 11/2016 | Alsaud et al. |
| 2016/0342750 A1 | 11/2016 | Alsaud et al. |
| 2016/0342751 A1 | 11/2016 | Alsaud et al. |
| 2017/0091397 A1 | 3/2017 | Shah et al. |
| 2017/0103164 A1 | 4/2017 | Dunlevy et al. |
| 2017/0103165 A1 | 4/2017 | Dunlevy et al. |
| 2017/0132621 A1 | 5/2017 | Miller et al. |
| 2017/0372300 A1 | 12/2017 | Dunlevy et al. |

OTHER PUBLICATIONS

Bhattacharya, Indrajit and Getoor, Lise, *Entity Resolution In Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, © 2003, American Association for Artificial Intelligence (www.aaai.org) (6 pgs.).

Coleman et al., *Medical Innovation—a diffusion study*; The Bobbs-Merrill Company, Inc., 1966 (248 pgs.).

Domingos et al., *Mining High-Speed Data Streams*, (2000) (10 pgs.).

Greenhalgh et al., *Diffusion of Innovations in Health Service Organisations—a systematic literature review*, Blackwell Publishing, 2005 (325 pgs.).

Jackson et al., *The Evolution of Social and Economic Networks*, Journal of Economic Theory 106, pp. 265-295, 2002 (31 pgs.).

Jackson, Matthew O., *Social and Economic Networks*, Princeton University Press, 2008 (509 pgs.).

(56) References Cited

OTHER PUBLICATIONS

Krempl et al., *Open Challenges for Data Stream Mining Research*, SIGKDD Explorations, vol. 16, Issue 1, Jun. 2014 (64 pgs.).
Lin et al., *A simplicial complex, a hypergraph, structure in the latent semantic space of document clustering*, © Elsevier, 2005 (26 pgs.).
Rebuge, *Business Process Analysis in Healthcare Environments*, 2011, Ellsevier Ltd., pp. 99-116 (18 pgs.).
Wasserman et al., *Social Network Analysis: Methods and Applications*, Cambridge University Press; 1994 (434 pgs.).
White et al., *Algorithms for Estimating Relative Importance in Networks*, Proceedings of the Ninth ACM SIGKDD International Conference on Knowledge Discovery and Data Mining, 2003 (10 pgs.).
(MATHJAX), *Naive Bayes Categorisation (with some help from Elasticsearch)*, blog post dated Dec. 29, 2013 (https://blog.wtf.sg/2013/12/29/naive-bayes-categorisation-with-some-help-from-elasticsearch/). (8 pgs.).
Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010andD0/downloads/w5010BasicsFctCht.pdf (4 pgs.).
Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).
Anonymous: "Oauth—Wikipedia", Sep. 23, 2013. Retrieved from the Internet URL:https://en.wikipedia.org/w/index.php?title+oAuth&oldid+574187532.
Version 5010 and D.0, Center for Medicare and Medicaid Services (2 pgs.).
Anonymous: "Oauth" Wikipedia—Retrieved from the Internet URL:https://en.wikipedia.org/wiki/Oauth (8 pgs.).

\* cited by examiner

Recent Claims

| Statement Date ▼ | Insurance Provider ▼ | Status ▼ | |
|---|---|---|---|
| 2015-12-23 | APS Healthcare, Inc. | 7 warnings | view details |
| 2015-12-15 | Care Improvement Plus | 3 suggestions | view details |
| 2015-10-07 | Harmony Health Plan | 1 suggestion | view details |
| 2015-09-30 | Medical Mutual of Ohio | Claim meets recommendations | view details |
| 2015-09-24 | Medical Mutual of Ohio | Claim meets recommendations | view details |

Claim Details

ⓘ There are four critical fixes and three warnings recommended for this claim.

CPT Notices
- CPT Codes 80352 and 88182 are considered duplicative and are not accepted in the same claim.
- CPT Codes 80352 and 97811 are possibly duplicative and are rarely accepted in the same claim.

⎴ 602

| CPT | ICDs | Price |
|---|---|---|
| 80352 | W81.61XA<br>G25.81<br>W14.XXXA<br>S74.00XA | $700 (15%)<br>This price is significantly lower than the average for this CPT code. |
| 88182 | ICD not associated with CPT<br>W81.92XA | $500 (54%) |
| 97811 | T36.0X1A<br>W07.XXXA<br>W11.XXXA | $3200 (83%)<br>This price is significantly higher than the average for this CPT code. |

Claim Details

⚠ There are four critical fixes and three warnings recommended for this claim.

CPT Notices

- CPT Codes 00352 and 88102 are considered duplicative and are not accepted in the same claim.
- CPT Codes 00352 and 97811 are possibly duplicative and are rarely accepted in the same claim.

| CPT | ICDs | Price |
|---|---|---|
| 00352 | W51.61XA<br>G25.81<br>W14.XXXA<br>S74.00XA | $700 (15%) |
| 88102 | W51.92XA | $500 (54%) |
| 97811 | T36.0X1A<br>W07.XXXA<br>W11.XXXA | $3200 (83%) |

FIGURE 7

Claim Details

⚠ There are two warnings regarding this claim. See below for recommendations.

CPT Notices

- CPT Codes 00352 and 97811 are possibly duplicative and are rarely accepted in the same claim.

| CPT | ICDs | Price |
|---|---|---|
| 00352 | W51.61XA<br>G25.81<br>W14.XXXA | $1400 (59%) |
| 88102 | ICD G25.81 and W14.XXXA are rarely associated with CPT 00352 and may cause a rejection.<br>W51.92XA | $500 (54%) |
| 97811 | T36.0X1A<br>W07.XXXA<br>W11.XXXA | $1600 (51%) |

FIGURE 8

Claim Details

ⓘ There are four crucial fixes recommended for this claim. See below for recommendations.

CPT Notices

* CPT Codes 00352 and 97811 are considered duplicative and are not accepted in the same claim.

| CPT | ICDs | Price |
|---|---|---|
| 00352 | W61.61XA<br>G25.82<br>Q14.XXXA<br>S74.00XA | $700 (15%)<br>This price is significantly lower than the average for this CPT code. |
| 88102 | ICD not associated with CPT.<br>W61.92XA | $500 (54%) |
| 97811 | T36.0X1A<br>W07.XXXA<br>W11.XXXA | $3200 (83%)<br>This price is significantly higher than the average for this CPT code. |

FIGURE 9

Claim Details

ⓘ There are four critical fixes and three warnings recommended for this claim.

CPT Notices

* CPT Codes 00352 and 88102 are considered duplicative and are not accepted in the same claim.
* CPT Codes 00352 and 97811 are possibly duplicative and are rarely accepted in the same claim.

| CPT | ICDs | Price |
|---|---|---|
| 00352 | W61.61XA<br>G25.81<br>W14.XXXA<br>S74.00XA | $700 (15%)<br>This price is significantly lower than the average for this CPT code. |
| 88102 | ICD not associated with CPT.<br>W61.92XA | $500 (54%) |
| 97811 | T36.0X1A<br>W07.XXXA<br>W11.XXXA | $3200 (83%)<br>This price is significantly higher than the average for this CPT code. |

SYSTEM AND METHOD FOR DYNAMIC HEALTHCARE INSURANCE CLAIMS DECISION SUPPORT

FIELD

The disclosure relates generally to a system and method for facilitating claims processing in a healthcare environment.

BACKGROUND

According to the American Medical Association, administrative costs associated with the processing of health care insurance claims is upwards of $210 billion per year in the United States. The AMA also estimates that as many as 1 in 5 claims is processed inaccurately leading to significant amounts of money lost due to waste, fraud, and abuse. Three major reasons that claims are not processed by payers are:
  Procedures are charged for a dollar amount greater than the payer's allowed amount for that procedure
  The diagnosis codes (ICD9/10) are not sufficient to warrant the procedure.
  The combination of procedures in the claim is not valid, i.e. having 2 diagnostic tests that overlap.

Clinicians are increasingly adopting electronic clinical decision support tools to aid in determining their diagnoses. However, no system exists that provides healthcare provider billing personnel with the ability to discover abnormal claims and provide details on which constituent parts may need to be addressed so that the claim is adjudicated as desired.

DETAILED DESCRIPTION OF ONE OR MORE EMBODIMENTS

The disclosure is particularly applicable to processing claims and claim decision support using the X12 healthcare data application programming interfaces (APIs) and it is in this context that the disclosure will be described. It will be appreciated, however, that the system and method has greater utility because: 1) the system and method may be used to process claims information using other known or yet to be developed APIs and protocols; and 2) the system and method may be implemented differently than disclosed below, but those other, alternative implementations are within the scope of the disclosure.

The area of healthcare claims processing is presently at best mismanaged or misappropriated and is wrought with errors that require both manual and electronic processing efforts. The claim processing support system and method disclosed below allows for the pre-processing of the healthcare claims as well as the method to reduce much of this overhead and alerting the user to any errors that occur during the claims processing.

Figure 1:
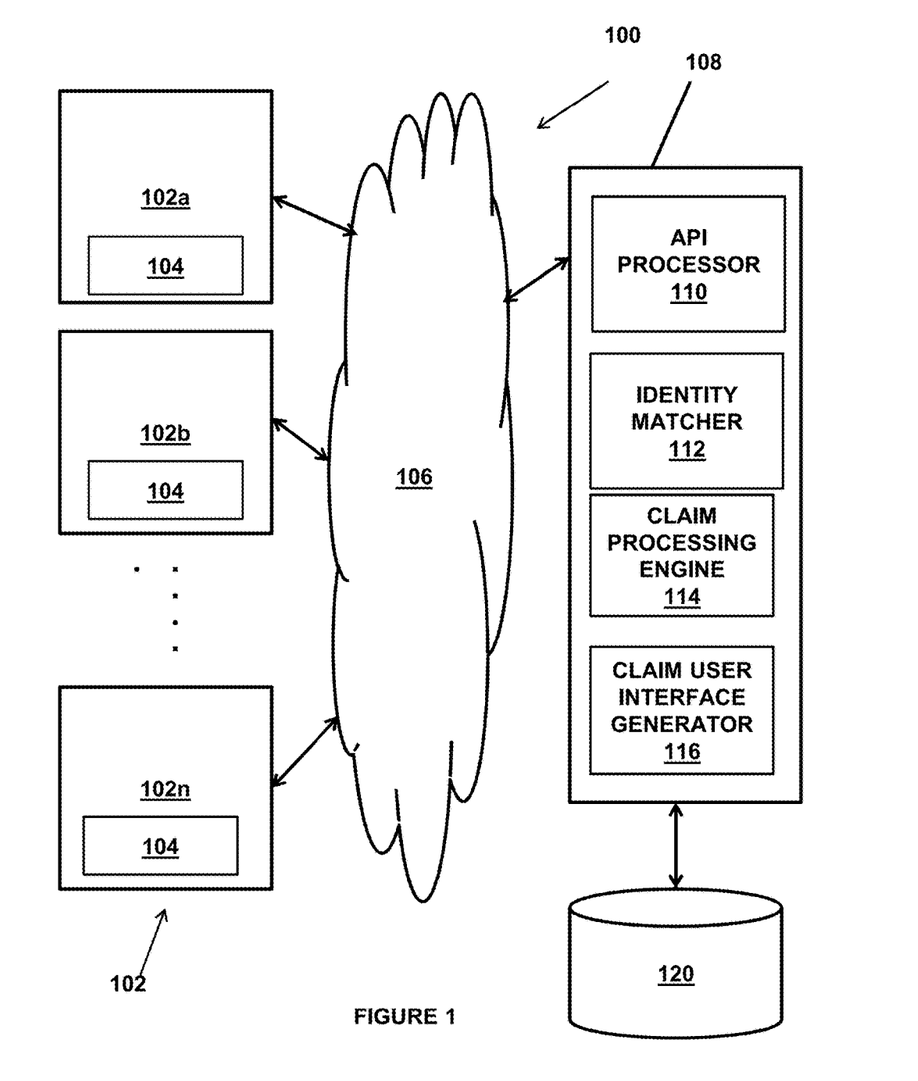
FIG. 1 illustrates an example of an implementation of a healthcare system that may include a healthcare claim decision support system.
Figure 5:
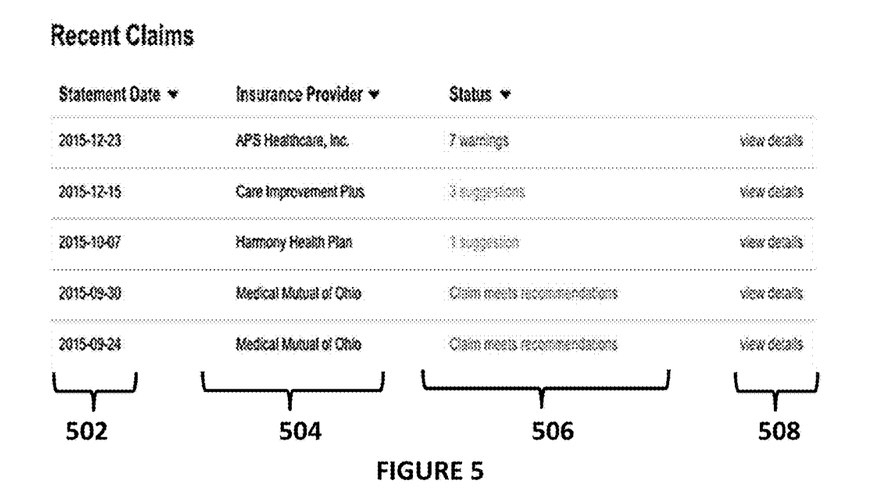
FIGS. 5 and 6 are examples of a healthcare claim user interface generated by the healthcare claim decision support system.
Figure 6:
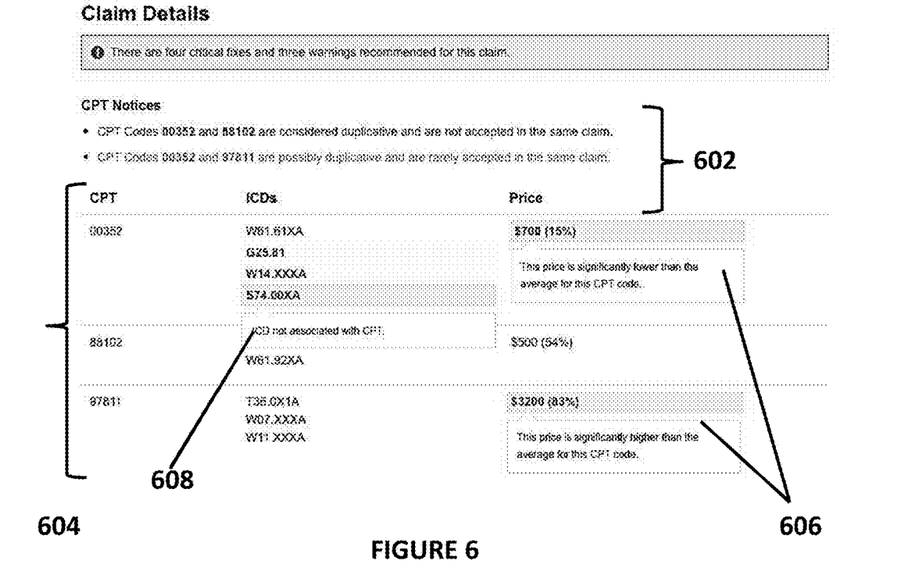

FIG. 1 illustrates an example of an implementation of a healthcare system 100 that may include a healthcare claim decision support system. The healthcare system may be used for various healthcare related purposes including healthcare claims processing and decision support. The system may have one or more computing devices 102, such as 102a, 102b, . . . , 102n as shown in FIG. 1, that permit a user to connect to and exchange data with the healthcare system and in particular the claims processing and decision support system. Each computing device may be a processor based device that has a display, memory, such as SRAM or DRAM, persistent storage, such as flash memory or a hard disk drive, typical input/output devices and communication circuits and software that allows each computing device to establish a connection with the healthcare system 108 and exchange data with the healthcare system 108 using various connection and data transfer protocols. For example, each computing device may be a smartphone device, such as an Apple iPhone or Android operating system based device, a personal computer, a tablet computer, a cell phone, a terminal device and a laptop computer. In one embodiment, each computing device 102 may have an application 104, such as a mobile application or typical browser application that may be executed by the processor of the computing device 102 to facilitate the connection to and interaction with the healthcare system backend 108 over a communication path 106. In one embodiment, the computing device may be used to exchange healthcare related data with the backend 108 including, for example user interfaces (examples of which are shown in FIGS. 5-6) for healthcare claim decision support as described in more detail below.

The communication path 106 may be a wired, wireless or a combination of wireless and wired communication paths that use various communication protocols and data transfer protocols to allow the computing devices 102 and the backend 108 to communicate with each other and exchange data with each other to perform the healthcare claim decision support. For example, in one implementation, TCP/IP and HTTPS or HTTP protocols may be used when a browser application is being used by the computing device 102. The communication path may be, for example, one or more of the Internet/World Wide Web, Ethernet, computer network, wireless data network, digital data network, Intranet, WiFi network and the like.

The backend 108 of the healthcare system may be implemented using one or more computing resources or cloud computing resources, such as one or more processors, one or more blade servers, one or more server computers and the like. The backend 108 may implement the claims decision support aspects using an application programming interface (API) processor 110, an identity matcher component 112, a claims processing engine component 114 and a claims decision support user interface component 116. Each of these components 110-116 may be implemented in hardware or software. If a component is implemented in software, the component may be a plurality of lines of computer code/instructions that may be executed by a processor of, for example, the healthcare backend 108, so that the processor is thus configured to perform the operations and functions of that component. If a component is implemented in hardware, the component may be an integrated circuit, gate array, microprocessor, microcontroller and the like that operate to perform the operations and functions of that component. A store 120 may be connected to the backend and may store various healthcare related data used by the system including, for example healthcare graph data, user healthcare data.

The API processor 110 may be a subsystem/component that processes and parses an incoming healthcare API data stream, such as an X12 healthcare data stream in one example, that is streaming into data that may be used for healthcare claim decision support. When the X12 healthcare data stream is being used, the API processor 110 may extract a healthcare eligibility response stream (a 271 stream), a healthcare claim submission stream (837 stream) and a claim payments stream (835 stream) from the X12 API streaming data. Further details of the API processing may be found in co-pending and commonly owned U.S. patent application Ser. No. 14/466,907, filed Aug. 22, 2014 and entitled "System and Method for Dynamic Transactional Data Streaming", which is incorporated herein by reference. The output of this API processing component 110 is used to perform the claim decision support and claims processing operations described below.

The identity matcher component 112 may be used to aggregate heterogeneous data in a time domain as described in more detail below with reference to FIG. 3. The claims processing engine component 114 may perform the healthcare claims processing and decision support operations on the healthcare claims data as described below in more detail. The claims decision support user interface component 116 may generate various user interfaces based on the healthcare claims support results. Examples of the user interfaces that may be generated by the system are shown in FIGS. 5-6 and described below in more detail.

Figure 2:
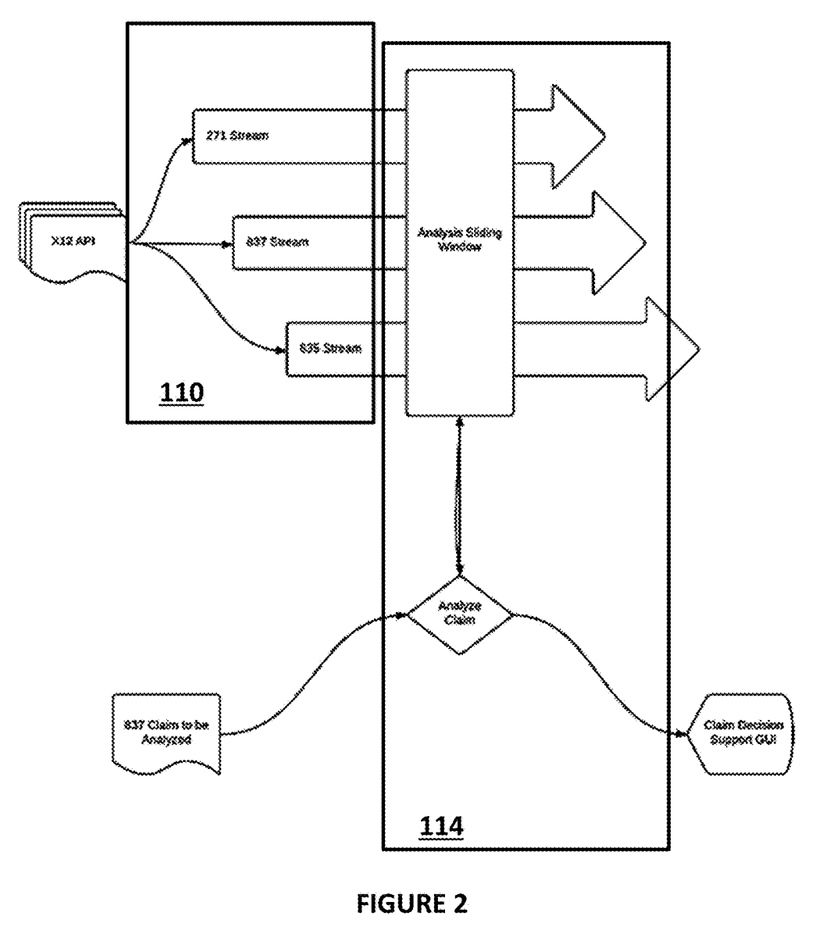
FIG. 2 illustrates more details of the healthcare claim decision support system.

FIG. 2 illustrates more details of the healthcare claim decision support system 108 that shows the processes performed by the API processor 110 and the claims processing engine component 114. The healthcare claim decision support system 108 may be considered a complex event processing architecture where the system and method transform streaming transactional data into a solution for providing claims decision support. In one implementation, the streaming healthcare data may be X12 API healthcare data since the current industry standard for electronic transmission of healthcare data is called HIPPA ASC X12 5010 per the Health Insurance Portability & Accountability Act (HIPPA) of 1996 (further details of which may be found at http://www.x12.org/x12org/subcommittees/x12n/n1100_hipaa_and_x12_-_intr.pdf).

For the healthcare claim decision support process, the API processor 110 may extract an eligibility responses data stream (271 stream in X12), a claim submissions data stream (837 stream in X12), and a claim payments data stream (835 stream in X12). Further, the identity matcher component 112 may match the heterogeneous data of the healthcare streams as described below in more detail with reference to FIG. 3.

837 Stream Analysis and Example

The 837 data stream may have various pieces of healthcare claims data.

Diagnosis Codes Per Procedure Code

Within the X12 837 file, each service for which a claim has been submitted is represented by an SV1 segment within the 2400—Service Line Number Loop. The SV1 segment contains the procedure code (usually a CPT code) and pointers for up to 4 diagnosis codes (usually either ICD9 or ICD10) for the service. An example SV1 segment may be:

SV1*HC:99211:25*12.25*UN*1*111:2:3Y~
HI*BK:8901*BF:87200*BF:5559~

Here the CPT code for the service is 99211 and the ICD9 codes are 89.01, 872.00, and 55.59. In the above example, CPT code 99211 pertains to an evaluation and management (E/M) service. The CPT manual defines code 99211 as an office or other outpatient visit "that may not require the presence of a physician. The example ICD9 codes correspond to Open wound of external ear, unspecified site, without mention of complication (872.00) and Interview and evaluation, described as brief (89.01).

Using the 271 stream, the 837 stream and the 835 stream, the claims processing engine component may perform a sliding window operation as shown in FIG. 2 that is used to aggregate, analyze, and correlate the Eligibility Responses (271), the Claim Submissions (837), and the Claim Payments (835) transactions in order to identify specific sections of the input 837 Claim that are abnormal. These issues are then presented to the user in a graphical user interface (GUI) (examples of which are shown in FIGS. 5 and 6) in a way that clearly denotes which parts of the claim are potentially problematic as well as a visual indication of the severity of the issue.

The Complex event processing (CEP) as described above is a method of tracking and analyzing streams of data from multiple sources and deriving real-time patterns. There are two major issues in dealing with multiple transaction streams (the various X12 streams in one embodiment) that the system and method addresses, namely:

1. Aggregation of Heterogeneous Data in a Time Domain
2. Concept Drift

Figure 3:
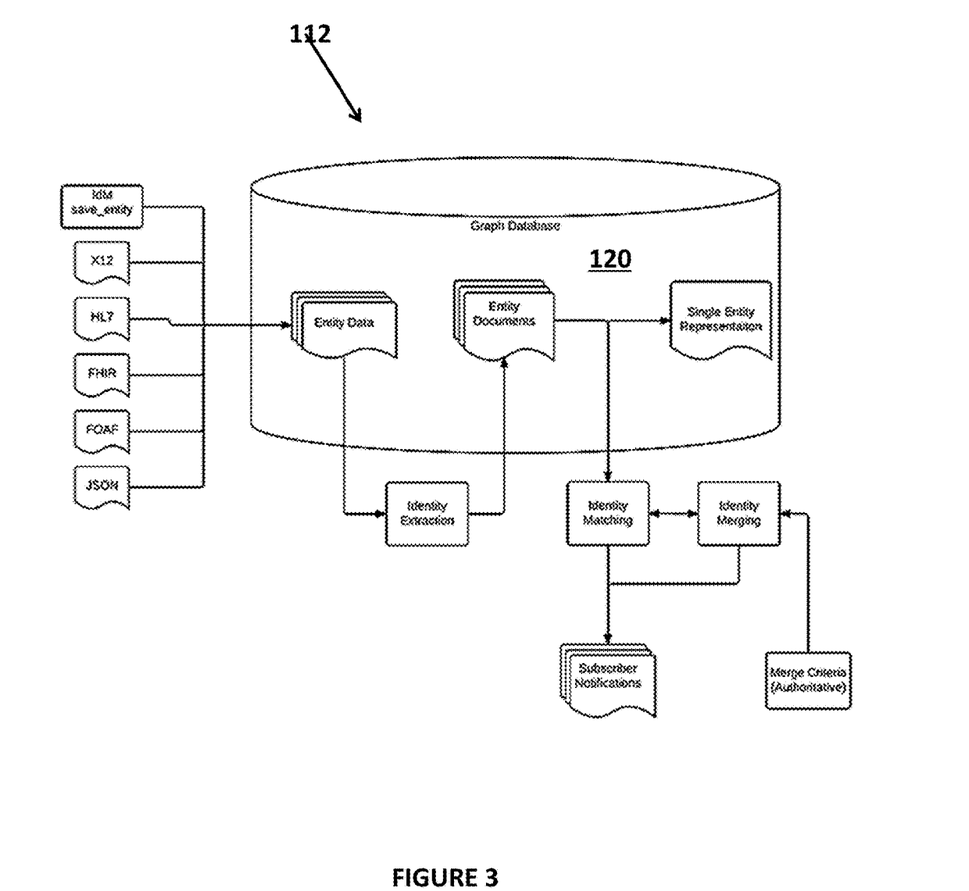
FIG. 3 illustrates an identity matching component that is part of the healthcare claim decision support system.

FIG. 3 illustrates the identity matching component 112 that is part of the healthcare claim decision support system that addresses the aggregation of heterogeneous data in a time domain. The usual process of events when a patient is seen is by a provider is:

1. A 270 Eligibility Request is sent when the patient registers at the provider's office and 271 Eligibility response is received that details the patient's current insurance status and explanation of benefits
2. The patient is seen by the provider (an "encounter")
3. An 837 Insurance Claim is sent by the provider to the payer for services rendered during the encounter.
4. The payer responds with an 835 Claim Payment message that details the amounts paid and any adjustments for the services listed in the 837.

In order to gain an accurate view of what happened in time for the events, the system aggregates the 271, 837, and 835 messages per encounter. An example of the aggregated 271, 837, and 835 messages for an encounter is contained in Appendix A that forms part of the specification and incorporated herein by reference. The system and method uses an extensive process for entity resolution to properly match the person to the encounter using the identity matching system shown in FIG. 3. Further details of the entity matching is described in co-pending and commonly owned U.S. patent application Ser. No. 14/884,703, filed Oct. 15, 2015 and Ser. No. 14/939,986, filed Nov. 12, 2015, both of which are titled "System And Method For Dynamic Autonomous Transactional Identity Management", the entirety of both of which are incorporated herein by reference.

Figure 4:
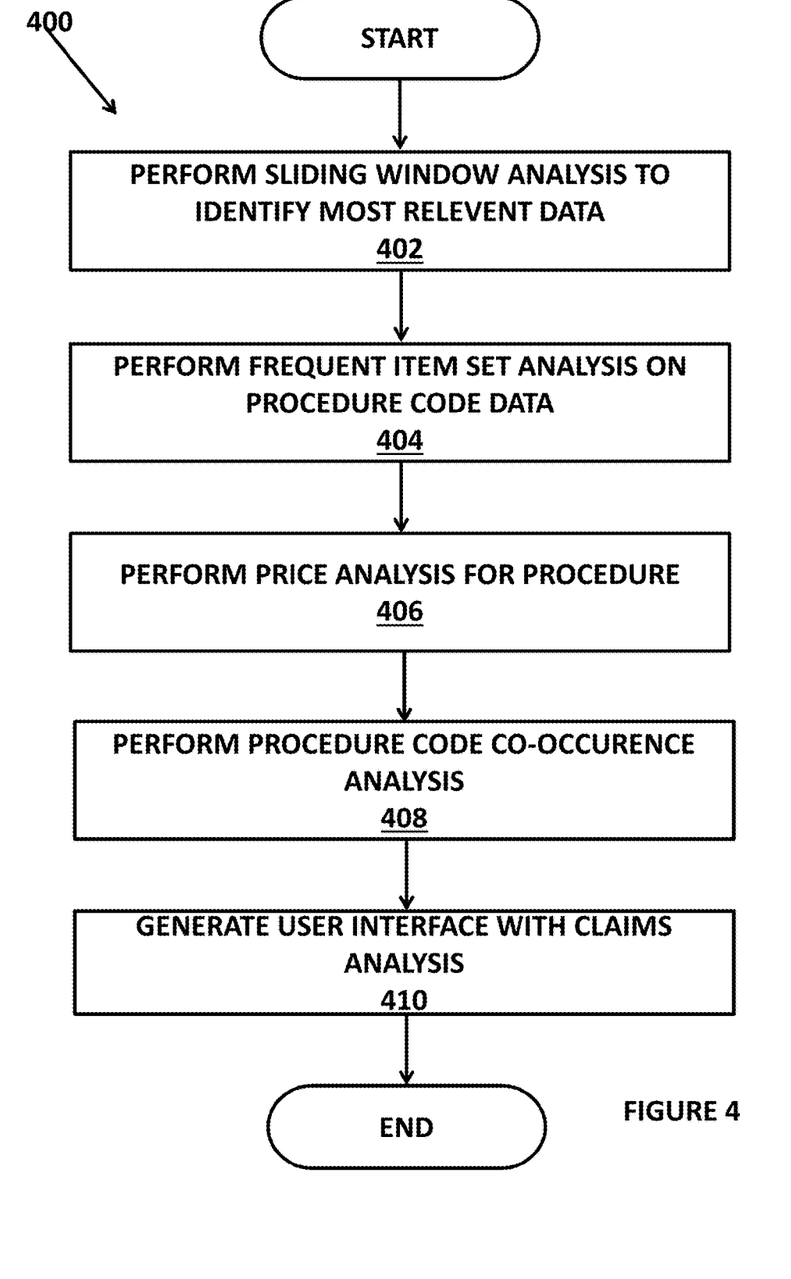
FIG. 4 illustrates a method for healthcare claim decision support processing.

FIG. 4 illustrates a method for healthcare claim decision support processing 400. In one embodiment, the method described below may be performed by the system shown in FIGS. 1 and 2, but the method may also be performed using other systems as well. As described above, one issue is concept drift that may be resolved by performing a sliding window analysis (402). Concept drift is a term used in machine learning and predictive analytics to describe the process by which the statistical properties of variables change over time in usually unforeseen ways. Specifically, when doing analysis of the healthcare data, such as aggregated X12 streams, there are many variables that drift with respect to time. As an example, the amounts that payers will pay for a given procedure change over time. In order to account for these phenomena, the method employs a parameterized sliding analysis window to the streams so that only the most relevant data is used in the respective analysis. For the example, the sliding window analysis may be implemented as follows:

```
def get_data_in_sliding_window(window_size):
    '''
    Returns encounter data from from today to 'window_size' days in
    the past.
    '''
    end_date = datetime.datetime.today( )
    start_date = end_date - window_size
    data = query_data(start_date=start_date, end_date=end_date)
    return data
window_data = get_get_data_in_sliding_window(30)
window_data.count( )
>> 36932
window_data = get_get_data_in_sliding_window(60)
window_data.count( )
>> 67231
```

Frequent Item Set Analysis

Using the most relevant data identified by the sliding analysis window process, the method 400 may perform a frequent item set analysis on the procedure data codes in the healthcare data streams (404). A common reason for service lines to be adjusted during adjudication is that the payer deems the procedure unwarranted with respect to the diagnoses. Association rule learning and frequent item set analysis are methods for discovering items that commonly appear together within a dataset of transactions. By applying these methods to the sliding window of healthcare data, such as the 271/837/835 messages, the method can determine which diagnosis codes are most frequently/infrequently associated to each procedure code and offer suggestions on possible missing or inappropriate diagnosis codes. The result of this analysis may be:

calc_cpt_cooccurrence_probibility(['99213', '29888'])
>>0.12

Since the probability is in the lowest quantile, the user would then see (as shown in FIG. 6, No. 602): "CPT codes 99213 and 29888 are rarely accepted in the same claim."

The frequent item set analysis process may be performed using several processes including:

Apriori—disclosed for example in Toivonen, Hannu. "Apriori Algorithm." *Encyclopedia of Machine Learning*. Boston: Springer US, 2010. 39-40. Print (that is incorporated herein by reference).

Elcat—disclosed for example in Mohammed Javeed Zaki, Srinivasan Parthasarathy, M. Ogihara, Wei Li: New Algorithms for Fast Discovery of Association Rules. KDD 1997 (that is incorporated herein by reference).

FP-Growth—disclosed for example in J. Han, H. Pei, and Y. Yin. Mining Frequent Patterns without Candidate Generation. In: Proc. Conf. on the Management of Data (SIGMOD'00, Dallas, Tex.). ACM Press, New York, N.Y., USA 2000 (that is incorporated herein by reference).

Below is an example of when the FP-Growth process is used to perform the frequency item set analysis process.

Example of FP-Growth Output

ICD9 codes for CPT code 99203=[["500.02", "890.0", "326.16"], ["500.02", "890.0"], ["234.0", "890.0", "432.09"]]

The results of the FT-Growth process may be:

| Itemset | Frequency |
| --- | --- |
| ['890.0'] | 3 |
| ['500.02', '890.0'] | 2 |
| ['500.02'] | 2 |
| ['432.09', '890.0'] | 1 |
| ['432.09'] | 1 |
| ['326.16', '890.0'] | 1 |
| ['326.16', '500.02', '890.0'] | 1 |
| ['326.16', '500.02'] | 1 |
| ['326.16'] | 1 |
| ['234.0', '890.0'] | 1 |
| ['234.0', '432.09', '890.0'] | 1 |
| ['234.0', '432.09'] | 1 |
| ['234.0'] | 1 |

Using the frequencies resulting from the frequent item set mining process above, the method can then calculate the probability:

$$P(CPT|ICD_1, ICD_2, \ldots, ICD_n)$$

The probability calculates how supported the CPT code is given the diagnosis codes, i.e. how "well" the provider has made their argument to charge for the procedure. The probability is then used to show a message that can be seen in FIG. 6, No. 608 as described below.

Procedure Price Analysis

Returning to FIG. 4, the method 400 may also perform a price analysis per procedure code and per payer (406) that identifies procedure prices in a claim that are abnormal (either too high or too low relative to a price usually paid by a particular payer for the procedure). Each SV1 services segment (as described above) contains the amount the provider is charging for the service in the SV102 field. For example, the SV1 segment may be:

SV1*HC:99211:25*12.25*UN*1*111:2:3Y~

In this example the procedure represented by CPT code 99211 is being charged $12.25 USD by the healthcare services provider (e.g., a doctor, a nurse, a clinic or healthcare professional).

In healthcare claims adjudication, service lines may be adjusted by payers if the charge amount exceeds the payer's allowed amount for the service. This allowed amount is not known to providers unless they have agreed to a contracted rate for the service with the healthcare services payer (e.g., an insurance company). The charged price for the service may be analyzed by determining what percentile the charged price falls in based on the charged prices for the CPT code and payer in the 837 sliding window.

Charged Price Example

Charged Prices for CPT 99203 for Payer A=[127.26, 160.49, 129.31, 129.90, 168.09, 149.45, 202.16, 135.24, 100.21, 127.23]

Charged Price in 837 being analyzed=$169.23 and the Payer for this claim is Payer A Using the above charged prices for Payer A, the following percentages may be determined:

| Percentile | Price |
|---|---|
| $5^{th}$ | $112.37 |
| $25^{th}$ | $127.77 |
| $50^{th}$ | $132.57 |
| $75^{th}$ | $157.73 |
| $95^{th}$ | $186.83 |

In the example above, the percentage is determined based on the prices for Payer A. However, if a different claim being analyzed was being adjudicated by Payer B, then Payer B's prices for the same procedure would be used instead. Thus, for each claim and each procedure, the percentiles of the prices for that procedure for the particular payer may be determined.

In this example, the charged price of $169.23 in the claim being analyzed is above the 75th percentile and below the 95th percentile of $186.83. Accordingly, in this example, the user may be alerted that their charged price is on the higher end for this CPT for this specific payer. An example of the user interface that shows this alert is shown in FIG. 6.

Procedure Code Co-Occurrence

Returning to FIG. 4, the method may also perform a procedure code co-occurrence analysis (408) to identify when multiple services are filed with a single claim. Specifically, multiple services can be filed within a single claim, but payers often have unpublished rules for which services can be billed within the same claim. As an example, for Medicare/Medicaid claims, the CPT code 64450 which is for a nerve block injection cannot appear in a claim where the CPT code 12001 for a laceration repair is also present.

In addition to reimbursement amounts for each service, the 835 payment file enumerates the reasons that a service line was adjusted by the payer. Using corresponding 837 and 835 files from the sliding window under analysis, the method can predict which services will be adjusted due to the combination of CPT codes in the claim. An example of the data in the various healthcare X12 data streams may be found in Appendix A.

In machine learning and statistics, classification is the problem of predicting to which set of categories a new observation belongs based on training data of instances whose category membership is already known. Using the 837/835 data steam pairs, the method may construct a training set of CPT code sets and assign them either to the class of code sets that are allowed to exist in a claim for a given payer or not.

Example Training Data

An example training set may be:
{'cpt_codes': ['99213', '99203'], 'payer': 'aetna', 'allowed': False}
{'cpt_codes': ['99213', '99203'], 'payer': 'united', 'allowed': True}
{'cpt_codes': ['99213', '74177'], 'payer': 'united', 'allowed': False}

Once the training set is constructed, the method can then train a classifier process to predict whether or not the set of CPT codes in the current claim under review are valid co-occurrences. Multiple algorithms exist for creating classifiers that may be used in different embodiments of the method, including but not limited to:
Logistic Regression
Support Vector Machines (SVM)
Random Forests of Decision Trees
Neural Networks
For example, the classify code example may be:

classify_cpt_codes({'cpt_codes': ['99213', '74177'], 'payer': 'united'})
>> 'not_allowed'
classify_cpt_codes({'cpt_codes': ['99213', '99203'], 'payer': 'united'})
>> 'allowed'

As a result of this analysis, the system may generate a user interface such as shown in FIG. 6 that says "ICD not associated with CPT" indicating a code that is not allowed in the claim.

User Interface Generation

Returning to FIG. 4, the method may generate one or more user interfaces (410) based on the above processes 402-408. For example, the method may generate the user interfaces shown in FIGS. 5-6. The user interfaces alert a human to possible issues in an 837 message before it is submitted to a payer for adjudication. The user interface accomplishes the following goals:
Identifies precisely what section(s) of the claim appear to be abnormal.
Presents the user with a clear with an indication of "severe" the abnormality is for each identified section.
Articulates the reason that each identified section was labeled as such.
When possible, offers suggestions on how to potentially correct the issue.

One such possible interface is to use a color coding (as shown in FIGS. 5-6) to identify abnormalities while at the same time conveying the severity of the abnormality.

FIG. 5 shows a claim summary user interface that, for each claim submitted to the claim decision support system and method, may have a statement date portion 502, an insurance provider (payer) for the particular claim portion 504, a status portion 506 and a view details portion 508. The status portion 506 shows the decision support status of each claim, such as 7 warnings, 3 suggestions or claim meets recommendations. The view details portion 508 permits the user to drill down to a lower level of the data such as shown in FIG. 6.

As shown in FIG. 6, the more detailed user interface for a particular claim may include a CPT code notices portion 602 and a detailed analysis portion 604 for each CPT code in a particular claim. The CPT code notices portion identifies CPT codes that may not be accepted in the same claim that is identified based on the procedure co-occurrence process described above.

The detailed analysis portion 604 for each CPT code may include various indications of problems with the claim. For example, this portion of the user interface may list a price issue 606 that may be identified based on the price analysis process described above and/or an incorrect ICD code for a particular CPT 608 that may be identified by the frequent item set analysis described above. In addition to the example user interfaces described above, the user interface may recommend ICD codes to include/remove for a CPT code.

Figure 7:
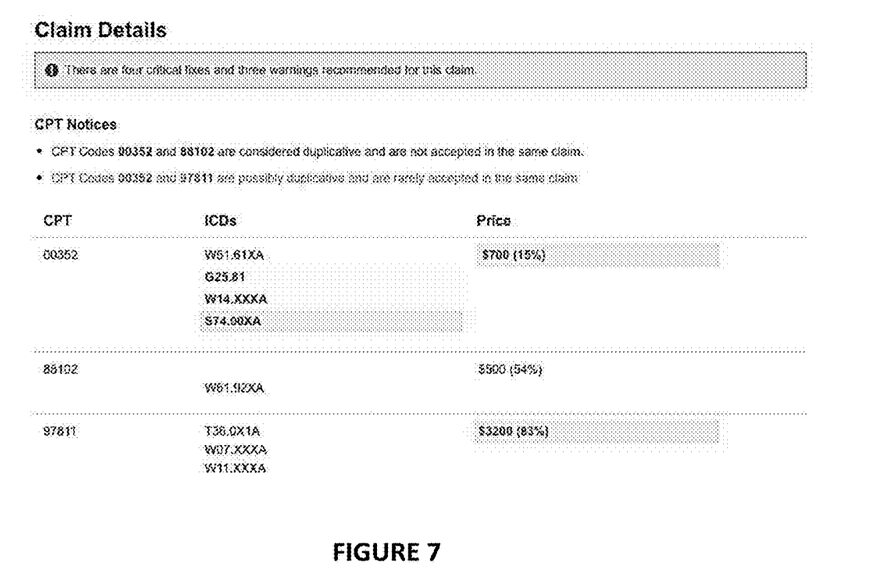
FIG. 7 is an example of the healthcare claim user interface generated by the healthcare claim decision support system showing warning and a critical fix of the claims as a result of the price analysis and the code co-occurrence analysis.

FIG. 7 is an example of the healthcare claim user interface generated by the healthcare claim decision support system showing warning and a critical fix of the claim. The user interface is generated as a result of the price analysis (showing the price being significantly higher or lower). The user interface is also generated based on code co-occurrence analysis that the particular ICD listed in the claim is not associated with the CPT code in the claim.

Figure 8:
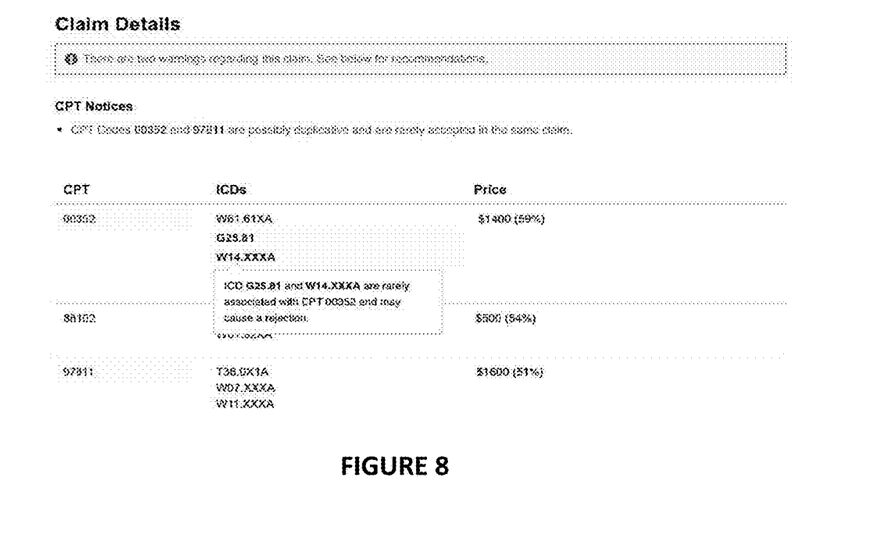
FIG. 8 is an example of the healthcare claim user interface generated by the healthcare claim decision support system showing warning as a result of the code co-occurrence analysis
Figure 9:
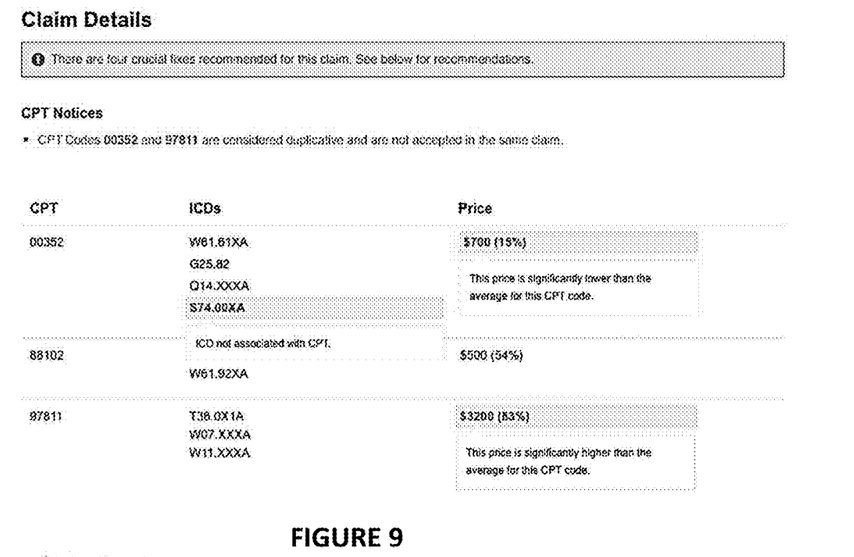
FIG. 9 is an example of the healthcare claim user interface generated by the healthcare claim decision support system showing critical issues as a result of the price analysis and the code co-occurrence analysis.
Figure 10:
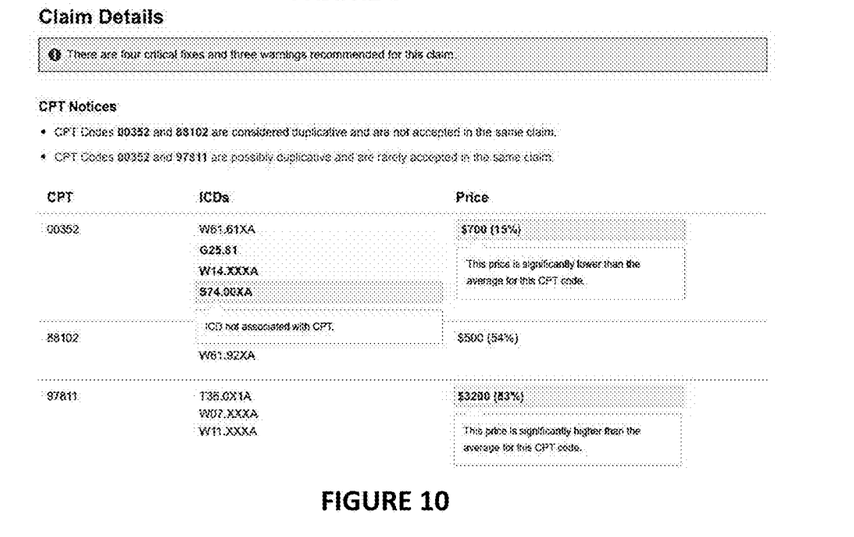
FIG. 10 is an example of the healthcare claim user interface generated by the healthcare claim decision support system showing a warning and a critical issue as a result of the price analysis and the code co-occurrence analysis.

FIG. 8 is an example of the healthcare claim user interface generated by the healthcare claim decision support system showing warning as a result of the code co-occurrence analysis in which the ICD codes in the claim are rarely associated with the particular CPT code in the claim. FIG. 9 is an example of the healthcare claim user interface generated by the healthcare claim decision support system showing critical issues as a result of the price analysis and the code co-occurrence analysis. FIG. 10 is an example of the healthcare claim user interface generated by the healthcare claim decision support system showing a warning and a critical issue as a result of the price analysis and the code co-occurrence analysis.

Example Implementation of the Decision Support Method

Figure 11:
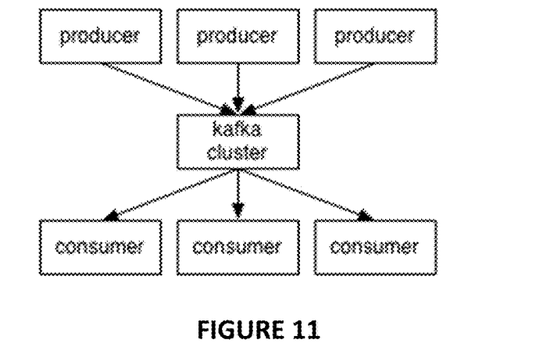
FIG. 11 illustrates a Kafka implementation of the healthcare claim decision support system.

The above method may be implemented in various different ways. In one implementation, streams using Kafka may be used. FIG. 11 illustrates a Kafka implementation of the healthcare claim decision support system. Kafka is an open source message broker developed within the Apache Software Foundation. Kafka provides a unified, high throughput, low latency platform for handling real time data streams. Kafka maintains streams of messages in categories called topics and the processes that publish messages to a Kafka topic are called producers. Consumers subscribe to topics and process the stream of published messages as shown in FIG. 11.

Example of X12 Kafka Producer

```
from pykafka import KafkaClient
client = KafkaClient(hosts=kafka_url)
def produce_x12_msg(x12_msg_type, x12_msg):
    x12_topic = client[x12_msg_type]
    with x12_topic.get_sync_producer( ) as x12_producer:
        x12_producer.produce(x12_msg)
```

Example of X12 Kafka Consumer

The consumers of the X12 Kafka message streams use an offset to only fetch the messages that are within the temporal sliding analysis window.

```
def consume_x12_messages(x12_msg_type, sliding_window_offset):
    x12_topic = client[x12_msg_type]
    messages = list( )
    consumer = topic.get_balanced_consumer(x12_msg_type, offset=sliding_window_offset)
    for message in consumer:
        messages.append(message)
    return messages
```

Frequent Item Set Analysis Implementation Example

Figure 12:
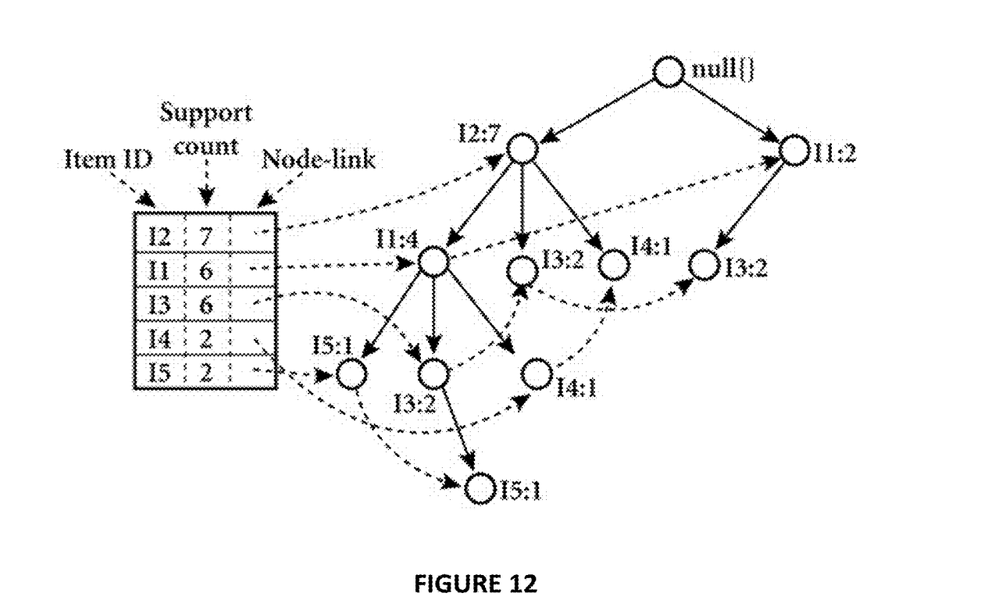
FIG. 12 illustrates an example of an FP tree example that may be used by the healthcare claim decision support system.

FIG. 12 illustrates an example of an FP tree example that may be used by the healthcare claim decision support system. More specifically, a function that trains an FP-Growth model to mine frequent ICD9/10 itemsets for a given CPT code from a sliding window may be:

```
from pyspark.mllib.fpm import FPGrowth
def get_frequent_item_sets(cpt_code, sliding_window_offset):
    messages = consume_x12_messages('837', sliding_window_offset)
    messages_rdd = sc.parallelize(messages)
    cpt_messages = messages_rdd.filter(lambda msg: get_cpt_code(msg) == cpt_code)
    diagnosis_codes = cpt_messages.map(lambda msg: get_diagnosis_codes(msg))
    model = FPGrowth.train(diagnosis_codes, minSupport=0.6)
    frequent_itemsets = model.freqItemsets( ).collect( )
    return frequent_itemsets
```

Example Implementation of FP-Growth Training Algorithm

FP-Growth is a method for determining frequent itemsets that is more efficient than Apriori since it does not rely on candidate generation and instead uses a frequent pattern tree (FP-tree) which encodes the itemset association information.
The algorithm works as follows:
1. It compresses the input transaction set and creates an FP-tree instance to represent the frequent itemsets.
2. It then divides the compressed transaction set into a collection of conditional transaction sets, each of which are associated with one frequent pattern.
3. Each transaction set is mined in parallel.

FP-Tree Structure
The FP-tree is structured as follows:
The root node of the tree is labeled as "null" and the children are a set of item prefix subtrees as well as a frequent item header table.
Each node in an item prefix subtree is composed of:
   Item Name: Associates which item is represented by the node.
   Count: The number of transactions represented by the portion of the path reaching the node.
   Node edge: A pointer to the next node in the FP-tree carrying the same item name or a null value.
Every entry in the frequent item header table consists of two values:

Item Name: Same as in the nodes
Head of Node Edge: A pointer to the first node in the FP-tree carrying the item name.
The frequent item header table may also contain the count support for an item.
An example of an FP tree is shown in FIG. 8.
FP-Tree Construction Algorithm
Input: A set of transactions and a minimum support threshold
Output: FP-tree
Method:
1. Iterate through the transaction set once. Collect the set of frequent items, F, and the support of each frequent item. Let L be the set F sorted by support in decreasing order.
2. Create the root of an FP-tree, T, and label it as "null"
3. For each transaction in the transaction set:
   a. Select the frequent items in the transaction and sort them according to the order of L. Let the sorted frequent itemx list in the transaction be [p, P], where p is the first element and P is rest of the list. Call insert tree([p, P], T).
   b. The function insert tree works as follows. If T has a child node N such that N.item_name is p.item_name, then increment N.count by 1; otherwise create a new node N whose count is 1 and link it to T, then set the node edge to the nodes that have the same item name. If P is nonempty then call insert tree(P, N) recursively.
FP-Tree Growth Algorithm
Input: An FP-tree, T, representing a set of transactions
Output: The set of frequent itemsets
Method: call FP-growth(FP-tree, null)

```
Procedure FP-growth(Tree, a) {
(01) if Tree contains a single prefix path then // Mining single
prefix-path FP-tree {
(02) let P be the single prefix-path part of Tree;
(03) let Q be the multipath part with the top branching node replaced
by a null root;
(04) for each combination (denoted as β) of the nodes in the path P
do
(05) generate pattern β ∪ a with support = minimum support of
nodes in β;
(06) let freq pattern set(P) be the set of patterns so generated;
}
(07) else let Q be Tree;
(08) for each item ai in Q do { // Mining multipath FP-tree
(09) generate pattern β = ai ∪ a with support = ai .support;
(10) construct β's conditional pattern-base and then β's conditional
FP-tree Tree β;
(11) if Tree β ≠ ∅ then
(12) call FP-growth(Tree β , β);
(13) let freq pattern set(Q) be the set of patterns so generated;
}
(14) return(freq pattern set(P) ∪ freq pattern set(Q) ∪ (freq pattern
set(P) × freq pattern set(Q)))
}
```

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media.

Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

The healthcare claims processing system and method disclosed above improves the technical field of healthcare claim processing in which a computer processes healthcare claims. Specifically, unlike conventional healthcare claims processing systems that are fraught with errors and limitations, the disclosed healthcare claims processing system and method allows for the pre-processing of the healthcare claims as well as the method to reduce much of this overhead and alerting the user to any errors that occur during the claims processing. The disclosed system and method uses a novel analysis sliding window process and the algorithms disclosed to achieve the improved healthcare processing.

The healthcare claims processing system and method disclosed above apply abstract idea with machine, but not generic computer functions. While the system may perform data processing such as healthcare claims processing, the healthcare claim processing is being performed by a computer system that is performing more than just generic computer functions including the processing of X12 API data and performing a sliding window analysis of healthcare claims.

The healthcare claims processing system and method disclosed above also adds specific element that are other than well understood, routine and conventional in the field. Specifically, the system and method use a sliding window analysis of healthcare claims that is not well understood, routine and conventional in the field.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A method for healthcare claim decision support, comprising:
providing a computer with a processor, memory and a plurality of computer instructions configured to:
receive streaming transactional healthcare claim data;
extract a healthcare eligibility data stream, a healthcare claim submission data stream and a healthcare claim payment data stream from the streaming transactional healthcare claim data;
aggregate a message from the healthcare eligibility data stream, a message from the healthcare claim submission data stream and a message from the healthcare claim payment data stream about a particular claim being submitted to a payer;
perform a sliding window analysis to the aggregated messages about the particular claim being submitted to the payer to identify healthcare claim data in the aggregated messages that is relevant to the particular claim being submitted to the payer;
perform a frequent item set process on the identified healthcare claim data to determine a procedure code in the aggregated messages that does not match a service code;
perform a price analysis of the identified healthcare claim data in the aggregated messages to identify a price for a service or procedure in the claim that is abnormal for the payer;
perform a code co-occurrence of the identified healthcare claim data in the aggregated messages to identify two procedure codes that are not allowed in the same claim by the payer; and
generate user interfaces that show, for the particular claim to the payer, one or more issues with the claim based on the procedure code that does not match the service code, the price that is abnormal for the payer and two procedure codes that are not allowed in the same claim by the payer.

2. The method of claim 1, wherein performing the frequent item set process further comprises using an FP-Growth process to determine the procedure code that does not match the service code.

3. The method of claim 1, wherein performing the price analysis further comprises generating a price percentile for the payer for the procedure and comparing a price of the claim in the identified healthcare claim data to the price percentile for the payer.

4. The method of claim 1, wherein performing the code co-occurrence of the identified healthcare claim data further comprises using a classifier process to identify two procedure codes that are not allowed in the same claim by the payer.

5. The method of claim 1, wherein receiving the one or more healthcare data streams further comprises receiving an X12 271 steam, an 837 stream and an 835 stream.

6. The method of claim 1 further comprising processing one or more X12 API data streams to generate the one or more healthcare claim data streams.

7. The method of claim 1, wherein the procedure code is a CPT code and the service code is an ICD9 code.

8. An apparatus healthcare claim decision support, comprising:
a processor and a memory, the processor executing a plurality of lines of instructions that cause the processor to be configured to:
receive streaming transactional healthcare claim data;
extract a healthcare eligibility data stream, a healthcare claim submission data stream and a healthcare claim payment data stream from the streaming transactional healthcare claim data;
aggregate a message from the healthcare eligibility data stream, a message from the healthcare claim submission data stream and a message from the healthcare claim payment data stream about a particular claim being submitted to a payer;
perform a sliding window analysis to the aggregated messages about the particular claim being submitted to the payer to identify healthcare claim data in the aggregated messages that is relevant to the particular claim being submitted to the payer;
perform a frequent item set process on the identified healthcare claim data in the aggregated messages to determine a procedure code that does not match a service code;
perform a price analysis of the identified healthcare claim data in the aggregated messages to identify a price for a service or procedure in the claim that is abnormal for the payer;
perform a code co-occurrence of the identified healthcare claim data in the aggregated messages to identify two procedure codes that are not allowed in the same claim by the payer; and
generate user interfaces that show, for the particular claim to the payer, one or more issues with the claim based on the procedure code that does not match the service code, the price that is abnormal for the payer and two procedure codes that are not allowed in the same claim by the payer.

9. The apparatus of claim 8, wherein the processor is configured to use an FP-Growth process to determine the procedure code that does not match the service code.

10. The apparatus of claim 8, wherein the processor is configured to generate a price percentile for the payer for the procedure and compare a price of the claim in the identified healthcare claim data to the price percentile for the payer.

11. The apparatus of claim 8, wherein the processor is configured to use a classifier process to identify two procedure codes that are not allowed in the same claim by the payer.

12. The apparatus of claim 8, wherein the processor is configured to receive an X12 271 steam, an 837 stream and an 835 stream.

13. The apparatus of claim 8, wherein the processor is configured to process one or more X12 API data streams to generate the one or more healthcare claim data streams.

14. The apparatus of claim 8, wherein the procedure code is a CPT code and the service code is an ICD9 code.

* * * * *